United States Patent [19]

Gunter

[11] 4,256,132
[45] Mar. 17, 1981

[54] SAFETY DEVICE FOR CLAMP FOR MEDICAL SOLUTION ADMINISTRATION SYSTEMS

[76] Inventor: Richard C. Gunter, 93-40 Cullen Pkwy., Crisfield, Md. 21817

[21] Appl. No.: 967,166

[22] Filed: Dec. 7, 1978

[51] Int. Cl.³ ............................................. F17D 1/16
[52] U.S. Cl. ..................................... 137/14; 137/382; 251/6
[58] Field of Search .................. 251/6; 137/377, 382, 137/383, 384, 14; 29/157.1 R

[56] References Cited

U.S. PATENT DOCUMENTS

| | | | |
|---|---|---|---|
| 659,285 | 10/1900 | Boyle | 137/382 |
| 898,386 | 9/1908 | Nagle | 137/382 |
| 986,520 | 3/1911 | Tarr | 137/382 |
| 2,136,216 | 11/1938 | Martin | 137/384 |
| 3,685,787 | 8/1972 | Adelberg | 251/6 |
| 3,831,625 | 8/1974 | Roediger | 251/6 X |
| 3,885,562 | 5/1975 | Lampkin | 128/218 R |
| 3,980,099 | 9/1976 | Youngblood | 137/382 |

Primary Examiner—Harold W. Weakley
Attorney, Agent, or Firm—Walter G. Finch

[57] ABSTRACT

The invention is an improved safety method and device for clamps used in medical solution administration systems. The safety device is an effective cover for the operating mechanism of the clamp that forces the attendant medical person to take deliberate action to reach the operating mechanism. In so doing, the medical attendant is induced to first observe and read the label of the solution line to ascertain and assure selection of the proper feed line and then take the deliberate action of exposing the operating mechanism.

Thus, safety is inserted in the medical action to prevent careless selection of a solution line and improper setting of the valve clamp.

The safety device consists of a flap or cover over the mechanism that must be raised to operate the mechanism. A label on the device identifies the solution line involved so as to permit proper selection of the desired line.

17 Claims, 6 Drawing Figures

SAFETY DEVICE FOR CLAMP FOR MEDICAL SOLUTION ADMINISTRATION SYSTEMS

BACKGROUND AND SUMMARY OF THE INVENTION

The invention relates to safety devices and safety methods and in particular to safety devices for use in the medical profession. Specifically, it relates to safety devices and safety methods for medical solution administration systems.

In the prior art, numerous methods of clamping medical solution lines have been used. Some have merely been common pinch type clamps, other have had the capability of providing a partial clamping action to control the solution flow (varying from full flow to complete cut-off), None of these clamps have had any safety device connected with the clamp.

The present invention is designed to provide a device and method to assure safety in medical solution administration system for continuous intravenous therapy. From time to time there have been reported instances of near catastrophes in the administration of medical solutions.

Most present day clamps operate somewhat similarly. A wheel or roller-like element of the structure is moved by a finger or thumb of the operator up and down an inclined plane in order to wedge or squeeze a small tube. This squeezing compresses the tubing as the roller moves downward on the inclined plane and decompresses the tubing as the roller moves upward on the inclined plane. At various points between fully closed and fully open, the tubing has a relative graduated opening for adjusted flow. In other clamps, a roller operating on a more or less straight track merely closes or opens the passageway in the tubing. The roller may have short axle-like projections on each side and operate in track-like slots.

In any event, these clamp devices are subject to operation without any safety device to interrupt the operator or face the operator to take deliberate action to operate the clamp. Thus, in a plurality of medical solution administration lines to a patient, or even just a single such line to a patient, a medical attendant has no deterring force to cause the attendant to observe what line is selected or what adjustment is made. Merely reaching out and making an adjustment to a line could prove disastrous, perhaps fatal.

In the present invention the medical attendant is forced to deliberately remove the safety flap or cover and in so doing has the opportunity to observe the label on the line selected. Thus, a margin of safety is injected into the operation of the medical solution administration system.

The clamps are usually inserted on the tubing between the drip chamber from the medical solution supply and the injection structure at the injection site on the patient.

It is therefore an object of the invention to provide a method to induce safety into the routine of medical attention to the operation of medical solution administration systems.

It is another object of the invention to provide a safety device to force deliberate action by a medical attendant in operating a medical solution administration system.

It is a further object of the invention to provide a safety device to force deliberate attention by a medical attendant in selecting a medical solution line for ajustment in a medical solution administration system.

It is yet another object of the invention to provide a safety device that can be secured in place on the clamp structure of the medical solution administration system.

Further objects and advantages of the invention will become more apparent in light of the following description of the preferred embodiments.

DESCRIPTION OF THE PREFERRED EMBODIMENTS

Figure 1:
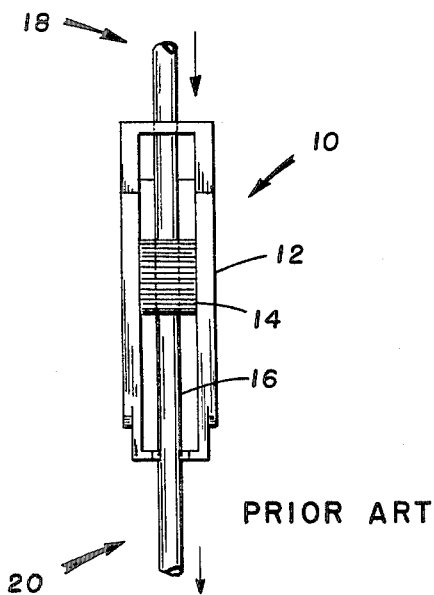
FIG. 1 is a front view of a typical clamp of the prior art.
Figure 2:
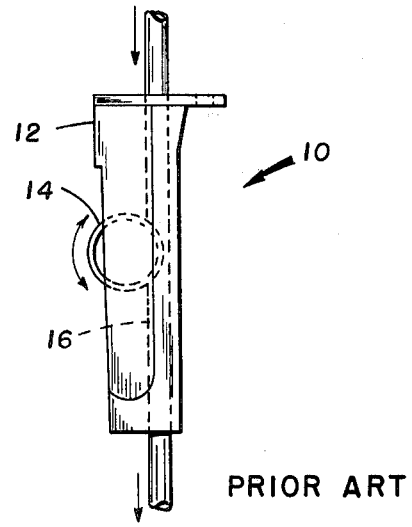
FIG. 2 is a sideview of a typical clamp of the prior art.

Referring to the drawings and particularly to FIGS. 1 and 2, a typical clamp of the prior art is shown at 10 for a medical solution administration system.

Figures 3, 4:
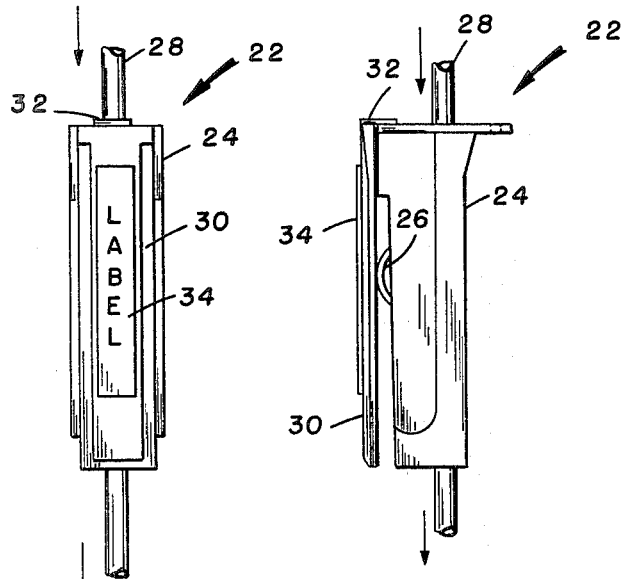
FIG. 3 is a front view of a labeled safety flap on a clamp.
FIG. 4 is a side view of a labeled safety flap on a clamp.

In FIGS. 3 and 4, a safety flap on a typical clamp is shown at 22 for a medical solution administration system.

There are variations in the existing clamps, but most have the structures for typical clamps 10 shown in FIGS. 1 and 2 for the prior art. In the prior art clamps 10, they are composed of a typical body 12 and a typical roller 14 that is held in and rolls up and down in a track-way within the body 12. As the roller 14 is rolled upward or downward in the track-way in the body 12, it compresses or decompresses the tubing 16 to control the flow of the medical solution passing through.

The tubing 16 is shown coming from the medical solution supply point at 18 in FIG. 1 and the tubing 16 is shown extending toward the patient at 20. The clamp 10 is normally placed on the tubing 16 of the medical solution administration system between the drip chamber (not shown) of the medical solution supply point at 18 and the injection structure (not shown) at the injection site on the patient at 20.

Turning now to FIGS. 3 and 4, a typical clamp with safety flap or cover is shown at 22. The safety flap or cover 30 is shown attached to a typical clamp body 24 by a hinge means 32. The safety flap or cover 30 can be seen covering the typical roller flow control 26 in the body 24. A label 34 is shown on the exterior side of the safety flap or cover 30.

The tubing 28 passes through the body 24 and under the roller 26 in the usual way. Arrows in FIGS. 3 and 4 indicate the direction of flow of the medical solution through the clamp with safety flap or cover 22.

It is to be noted that the clamp portion of the typical clamp with safety flap or cover 22 is similar to typical clamp 10 of the prior art. The structures of the clamps are also similar (body 12 and body 24, roller 14 and roller 26, and tubing 16 and tubing 28 passing through the clamps).

The flap or cover 30 may be of any suitable material, normally a material the same as the clamp body 24. The hinge means 32 may be a separate hinge or a hinge means that is integral with the flap or cover 30, or it may be integral with and monolithically formed or molded with both the flap or cover 30 and the clamp body 24.

Where the hinge means 32 is separate it may be suitably attached to the flap or cover 30 and the clamp body 24 by an adhesive or other suitable means.

Where the hinge means 32 is integral with the flap or cover 30 it may be suitably attached to the clamp body 24 by an adhesive or other suitable means.

It is to be undestood that other methods of providing a hinge means 32 is within the scope and intent of this invention.

The label 34 may be tape-like material adhesively attached to the flap or cover 30, on which the medical solution being used in the medical solution administration system may be written by the administering physical or medical attendant. The area of the label 34 on the flap or cover 30 may also be of a surface finish on which it is possible to write with pen or pencil as hereinbefore mentioned for the tape-like material.

It is to be understood that other methods of providing a label 34 on the flap or cover 30 is within the scope and intent of this invention.

Thus, in order for a medical attendant to adjust the flow of the medical solution flowing through the tubing 28, the medical attendant must first deliberately raise or lift the flap or cover 30 in order to operate the roller 26 in the body 24, instead of merely reading and making the adjustment. Thus, the added attention will induce added care, or safety, in making the adjustment.

It is to be noted that the configuration of the flap or cover 30 may be varied in size or shape as long as the flow control mechanism is covered. Such variations in the configuration are within the scope and intent of this invention.

A further safety measure is added in that the medical attendant is induced to read the label 34 to assure that the correct line 28 has been selected, particularly where may be a plurality of tubing lines 28.

Figure 5:
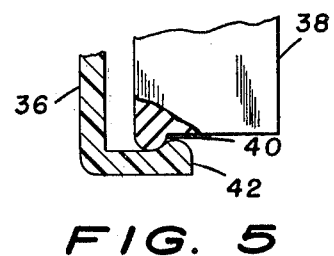
FIG. 5 is a partial side view and sectional view of a first embodiment of a retaining means on a safety flap.
Figure 6:
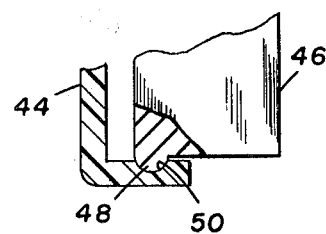
FIG. 6 is a partial side view and sectional view of a second embodiment of a retaining means on a safety flap.

As a further safety measure, the flap or cover 30 may have a snap-type fastening at the end as shown in FIGS. 5 and 6.

A first embodiment of a snap fit is shown in FIG. 5 where the flap or cover 36 has the free end turned or bent at 90° with a lip 42 on the end of the turned or bent portion. The lip 42 snaps over a companion lip 40 on the end of the clamp body 38. Thus, a medical attendant must positively take deliberate action to unsnap the flap or cover 36 in order to adjust the flow of medical solution as hereinbefore described. At the same time this positive deliberate action induces the attention of the medical attendant to read the aforementioned label. Thus, two safety actions are provided by this invention.

A second embodiment of a snap fit is shown in FIG. 6 where the flap or cover 44 has the free end turned or bent at 90° with a groove, slot, or recess 50 on the inboard face of the turned or bent end. The groove, slot, or recess 50 in the turned or bent end snaps over a mating lip 48 on the body 46. Thus, a medical attendant must positively take deliberate action to unsnap the flap or cover 44 in order to adjust the flow of medical solution as hereinbefore described. At the same time this positive deliberate action induces the attention of the medical attendant to read the aforementioned label. Thus, two safety actions are provided by this invention.

A third embodiment, not shown, is to provide the reverse of the structure shown in FIG. 6, whereby the groove or slot or recess is provided in the outer face of the body 46, and a lip is provided on the inboard face of the turned or bent end of the flap or cover 44. The lip in this embodiment would snap into the mating groove or slot or recess as hereinbefore described in reverse manner.

A fourth embodiment, not shown, is for the turned or bent end of the flap or cover 36 or 44 to merely fit over the end of the body 38 or 46 respectively in a friction fit.

Accordingly, modifications and variations to which the invention is susceptible may be practiced without departing from the scope and intent of the appended claims.

What is claimed is:

1. A method of providing safety in the operation of flow control clamps of medical solution administration systems having a tube-like connection from the medical solution supply to the patient with a flow control clamp situated along said tube-like connection, comprising, integrally and monolithically attaching one end of a safety cover to one end of a flow control clamp, laying said safety cover over an exposed operating mechanism in the body of said flow control clamp to prevent said operating mechanism from being exposed to ready access, and removably attaching by a snap fit juncture the other end of said safety cover to the other end of said flow control clamp so as to require deliberate delaying action to obtain subsequent access to said operating mechanism, thereafter inscribing the identification of a medical solution on a label on exterior of said safety cover thereby causing ready identification of said medical solution administration system when access to said operating mechanism is subsequently sought.

2. A safety device for a clamp for medical solution systems, comprising:

a medical solution administration system clamp, said clamp having a body member, said body member being hollow and of a rectangular prism-like configuration, said body member having one side of open and uncovered, said clamp body having a clamp operating mechanism assembled there in, said clamp operating mechanism being accessible through said opening for operation;

a cover means, said cover means being configured to cover said open side of said body member;

a hinge means said hinge means being integrally and monolithically attached to one end of said cover means and to one end of said clamp body means; and a medical solution identification means, said identification means being affixed to the exterior side of said cover means.

3. The safety device as recited in claim 2, wherein said cover means is a substantially flat plate-like structure that covers said open side of said clamp body member and said operating mechanism of said clamp in said body member.

4. The safety device as recited in claim 2, wherein said identification means is on a tape-like material adhesively attached to said cover means.

5. The safety device as recited in claim 2, wherein said identification means is on a writable surface integral with said cover means.

6. The safety device as recited in claim 2, wherein said cover means, with said hinge means attached to one end of said cover means and to one end of said clamp body means, has the other end of said cover means bent substantially at a right angle so as to interface with the other end of said clamp body means opposite to the hinge end thereof.

7. The safety device as recited in claim 6, wherein said bent end of said cover means interfaces with said other end of said clamp body means in a friction fit.

8. The safety device as recited in claim 6, wherein said bent end of said cover means and said other end of said clamp body means each have raised lips at the edges thereof to provide a snap fit.

9. The safety device as recited in claim 6, wherein said bent end of said cover means and said other end of said clamp body means alternatively have a mating lip and groove at the interface to provide a snap fit.

10. A safety device for a clamp for medical solution systems, comprising:
a medical solution administration system clamp, said clamp having a body member, said body member being hollow and of a rectangular prism-like configuration, said body member having one side thereof open and uncovered, said clamp body member having an operating clamp mechanism assembled therein, said clamp operating mechanism being accessible through said opening for operation;
a cover means, said cover means being configured to cover said open side of said body member;
a hinge means, said hinge means being integral with and monolithically formed to one end of said cover means, said hinge means then being affixed to one end of said body member by an adhesive means,
a medical solution identification means, said identification means being affixed to the exterior surface of said cover means.

11. The safety device as recited in claim 10, wherein said cover means is a substantially flat plate-like structure that covers said open side of said clamp body member and said operating mechanism of said clamp in said body member.

12. The safety device as recited in claim 10, wherein said identification means is on a tape-like material adhesively attached to said cover means.

13. The safety device as recited in claim 10, wherein said identification means is on a writable surface integral with said cover means.

14. The safety device as recited in claim 10, wherein said cover means, with said hinge means attached to one end of said cover means and to one end of said clamp body means, has other end of said cover means bent substantially at a right angle so as to interface with the other end of said clamp body means opposite to the hinge end thereof.

15. The safety device as recited in claim 14, wherein said bent end of said cover means interfaces with said other end of said clamp body means in a friction fit.

16. The safety device as recited in claim 14, wherein said bent end of said cover means and said other end of said clamp body means each have raised lips at the edges thereof to provide a snap fit.

17. The safety device as recited in claim 14, wherein said bent end of said cover means and said other end of said clamp body means alternatively have a mating lip and groove at the interface to provide a snap fit.

* * * * *

UNITED STATES PATENT AND TRADEMARK OFFICE
CERTIFICATE OF CORRECTION

PATENT NO. : 4,256,132
DATED : March 17, 1981
INVENTOR(S) : Richard C. Gunter

It is certified that error appears in the above—identified patent and that said Letters Patent is hereby corrected as shown below:

In the claims:

Claim 1, column 4, line 43, "of" should read --thereof--;

line 45, "there in," should read --therein,--.

Signed and Sealed this

Sixteenth Day of June 1981

[SEAL]

Attest:

RENE D. TEGTMEYER

*Attesting Officer*  *Acting Commissioner of Patents and Trademarks*